United States Patent [19]

Sen-Jung

[11] 4,065,815

[45] Jan. 3, 1978

[54] HYDRAULICALLY CONTROLLED ARTIFICIAL LEG

[76] Inventor: Chen Sen-Jung, 1st Floor No. 236-238, Section 3, Ho-Ping West Road, Taipei, China /Taiwan

[21] Appl. No.: 727,700

[22] Filed: Sept. 28, 1976

[51] Int. Cl.² .......................... A61F 1/04; A61F 1/08
[52] U.S. Cl. .............................................. 3/1.2; 3/23
[58] Field of Search ............................ 3/1.2, 2, 22–29

[56] References Cited

U.S. PATENT DOCUMENTS

| 2,667,644 | 2/1954 | Johnson | 3/1.2 |
| 2,671,224 | 3/1954 | Regnell | 3/1.2 |
| 3,069,692 | 12/1962 | Regnell | 3/1.2 |
| 3,800,333 | 4/1964 | Friberg | 3/23 X |

FOREIGN PATENT DOCUMENTS

| 530,887 | 10/1921 | France | 3/1.2 |

*Primary Examiner*—Ronald L. Frinks

[57] ABSTRACT

An artificial leg comprising a hydraulic system which is connected to a pushing rod of an ankle cap through a transfer rod, a foot which bears a recess to accept one end of the pushing rod and a knee part with its two ends separately connected to an outer shell and a pole means of the hydraulic system wherein the hydraulic system functions through a series of mechanical operations to automatically control the straightening and bending of the knee joint of the artificial leg.

6 Claims, 3 Drawing Figures

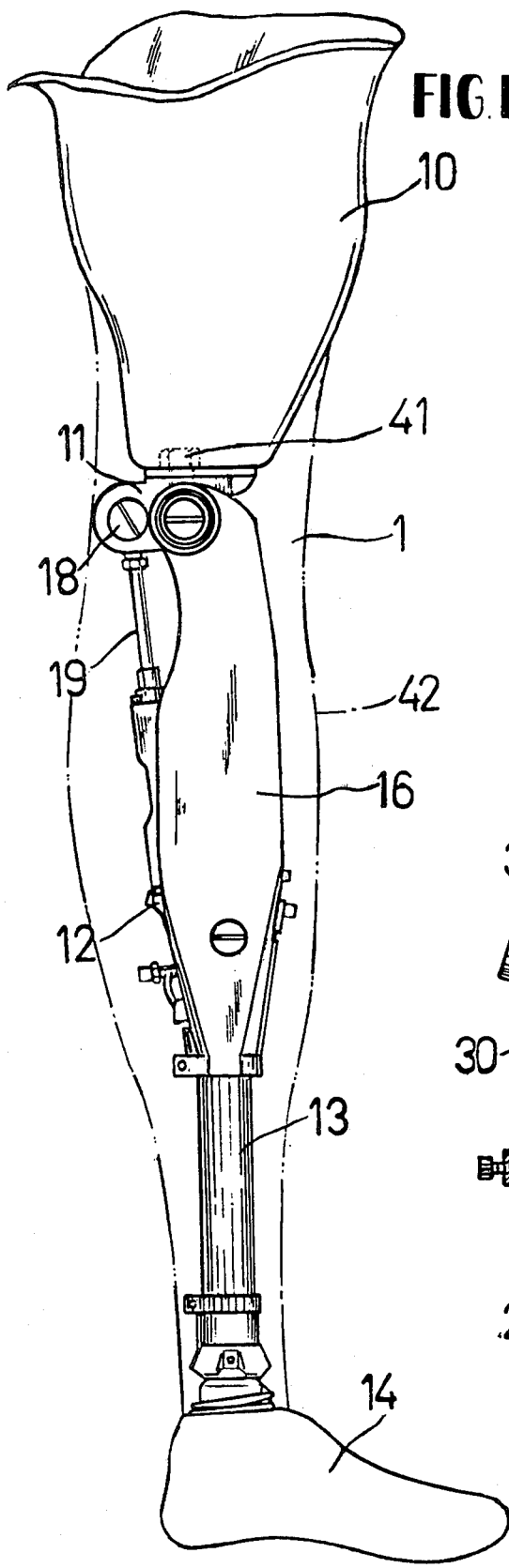
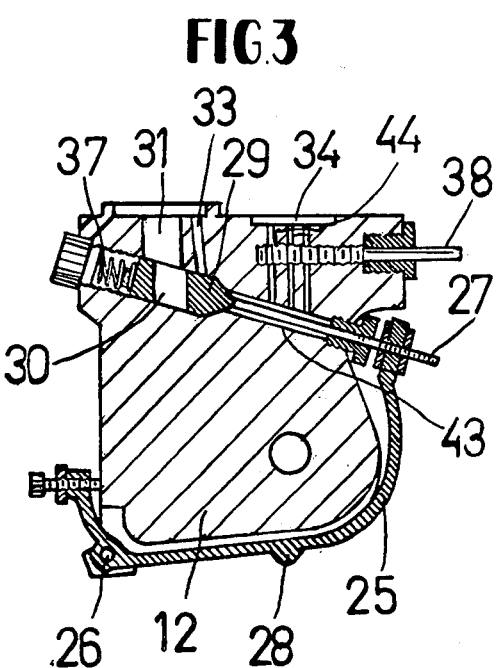

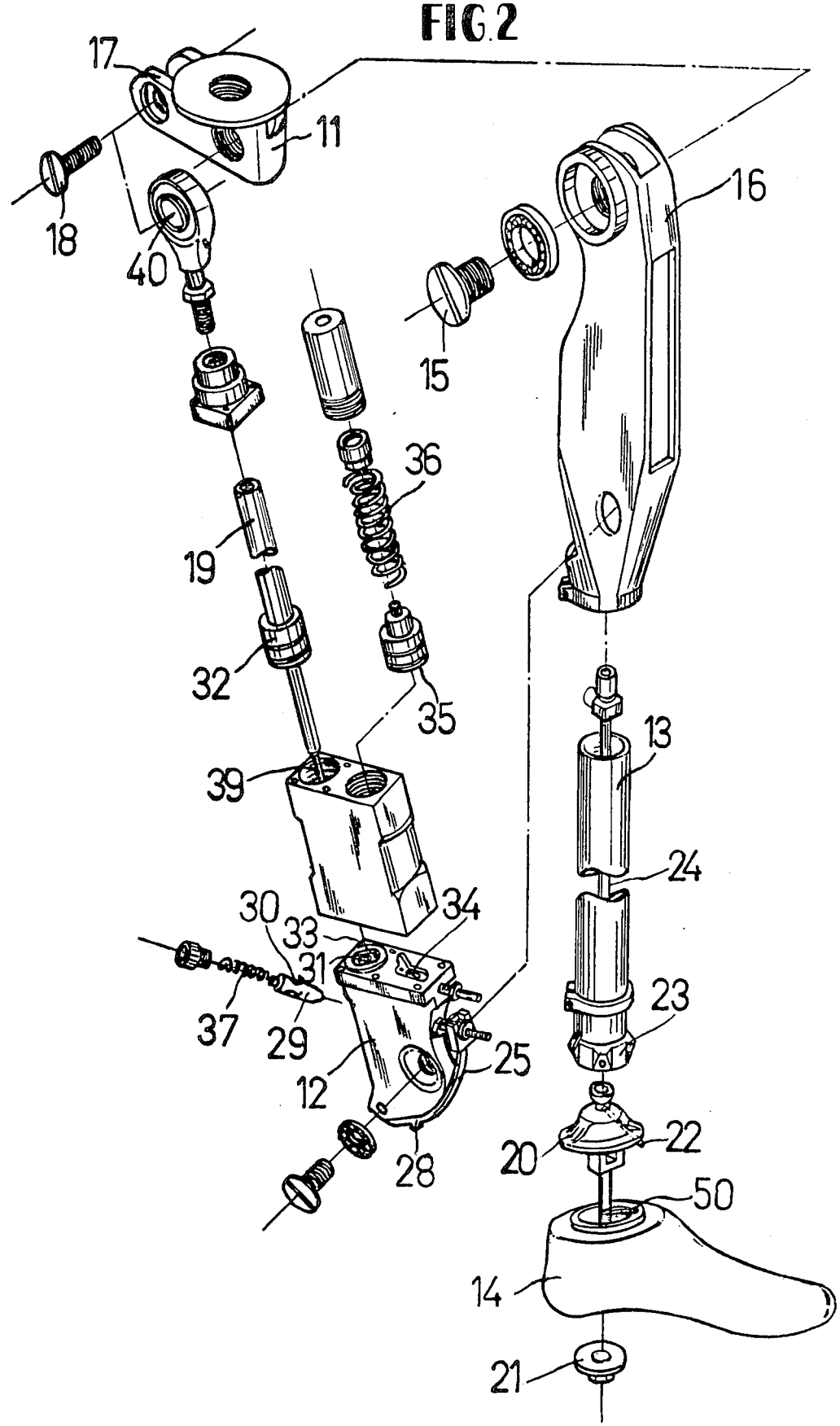

HYDRAULICALLY CONTROLLED ARTIFICIAL LEG

BACKGROUND OF THE INVENTION

Several different types of knee joints in an artificial leg have been known in the art, such as adaptor knee joint, linking clutch knee joint etc. In earlier stages, an artificial leg had only a few operating modes, e.g. free knee motion, stiff knee swing or safety knee motion mode. But none of the artificial legs can automatically change mode to enable it to operate suitably for all ground conditions.

Furthermore, an artificial leg with a conventional knee joint can not guarantee an amputee's safety when he is going downhill. Besides, the ankle portion between the foot and leg in a conventional artificial leg is fixed, thus making the amputee walk unsteadily.

BRIEF SUMMARY OF THE INVENTION

The object of the present invention is to provide a hydraulically controlled artificial leg wherein a pushing rod located in the ankle portion is depressed with respect to the foot movement to open a pet cock in said hydraulic system so as to automatically control the bending or straightening of the knee joint, thereby making the knee motions synchronous to the anke motions in both stance and swing phases.

Other objects and advantages of the present invention will become apparent from the following detailed description with reference to the accompanying drawings, wherein:

BRIEF DESCRIPTION OF THE DRAWINGS

FIG. 1 is a side view of the artificial leg according to the present invention;

FIG. 2 is an exploded view of the artificial leg according to the present invention; and FIG. 3 is a sectional view of the hydraulic system in the artificial leg according to the present invention.

DETAILED DESCRIPTION OF THE PREFERRED EMBODIMENT

Refer to FIG. 1 which shows a side view of the artificial leg according to the present invention. The artificial leg 1 comprises a thigh cover 10 attached to a knee 11 by a screw 41; a hydraulic system 12 connected to the knee 11 through a screw 18 and a pole means 19; a steel leg 13 extending between an outer shell 16 and a foot 14; and a properly shaped foam cover 42 covering the leg 1 to make the same to look like a real leg.

Refer to FIG. 2 which shows an exploded view of the artificial leg according to the present invention. One end of the knee 11 is connected to the outer shell 16 through a screw 15, and the other U-shaped end 17 is connected to said pole means 19 through a pivot 40 thus forming a movable knee joint. Provided on the foot 14, which is adapted to an ankle cap 20 by means of a nut 21, is a recess 50 to receive one end of a pushing rod 22 in said ankle cap 20. The other end of the pushing rod 22 pushes against a transfer rod 24 which passes through the central part of the steel leg 13. A hexagonal nut 23 is used to connect the steel leg 13 to the ankle cap 20. The foot 14 is capable of a slight back and forth motion thus forcing the pushing rod 22 upward to lift the transfer rod 24 which in turn pushes a transfer arm 25 at a protuberance 28, causing a counterclockwise rotation of the ram 25.

Refer to FIG. 3 which shows a sectional view of the hydraulic system in the artificial leg according to the present invention, and also refer to the hydraulic system 12 in FIG. 2. It is seen that a transfer arm 25 with a protuberance 28 formed thereon is pivoted upon a pin 26. Under normal circumstances, the steel leg 13 is vertical with respect to the ground, and the transfer rod 24 slightly touches the protuberance 28. A plug 29 with a first hole 30 formed thereon stopples an oil inlet 33 and the hole 30 is provided askew with respect to a second hole 31 thus only the leading needle part 39 of said pole means 19 can be inserted into the first hole 30. In this manner, when the amputee walks on a flat ground or downhill, the knee joint is always kept straight without bending due to the fact that said pole means 19 is fixed in position.

When walking uphill, the pushing rod 22 in the ankle cap 20 will push against the transfer rod 24, making the later push the transfer arm 25 counterclockwise. A link means 27 is driven to push the plug 29 back and open the oil inlet 33. In the meantime, the first hole 30 becomes in alignment with the second hole 31, whereby enabling the pole means 19 to fall down into the holes. A piston portion 32 of the pole means 19 compresses the hydraulic oil to pass through the oil inlet 33, passageways 43, 44, and an oil outler 34 into an oil chamber 33 and compress a spring 36. The oil flow rate can be adjusted by using a rotary adjuster 38. By said series of operations, the knee joint of the artificial leg is capable of bending smoothly, automatically and synchronously in accordance with the ankle motions. It is to be noticed that all the amputee has to do when he is walking on a flat surface and wants to bend his knee is to slightly move his foot forward, and the artificial leg according to the present invention will do the rest.

If the amputee steps back to a flat surface again, the pushing rod 22 will no more push the transfer arm 25. By the restoring force of the spring 36, the hydraulic oil will be compressed back to its original position. Meanwhile, the plug 29 will be forced back by means of the restitution force of a spring 37 to seal the oil inlet 33. The first and second holes 30, 31 become out of alignment again to straighten the knee joint of the artificial leg.

In summary, the artificial leg according to the present invention is a perfect, practical and novel one which can guarantee the amputee's safety.

What I claim is:

1. An artificial leg comprising a hydraulic system which is connected to a pushing rod of an ankle cap through a transfer rod; a foot bearing a recess receiving one end of the pushing rod; and a knee with its two ends separately connected to an outer shell and a pole means of the hydraulic system, wherein the hydraulic system comprises a transfer arm with a protuberance formed thereon and pivoted upon a pin; a plug for stoppling oil flow and having a first hole formed thereon; a link means connecting the transfer arm and the plug; a set of oil inlet, outlet, passageways and adjuster for oil flow, said pole means having one end connected to the knee through a pivot and the other end shaped into a needle part which is inserted into a second hole in the hydraulic system at least partially in alignment with the first hole on the plug; and a piston part on the pole means for compressing the hydraulic oil through said oil passageways into a chamber in the hydraulic system, so that the knee joint of the artificial leg can straighten or bend automatically and synchronously to the ankle motion through the hydraulic system.

2. A hydraulic system according to claim 1 wherein the adjuster for adjusting the oil flow in the oil passageways is a rotary one.

3. A hydraulic system according to claim 1 wherein under a straight knee joint circumstances, the plug is positioned so that the first hole is partially in alignment with the second hole whereby only the needle part of the pole means can be inserted into the holes.

4. A hydraulic system according to claim 3 wherein the plug is capable of being driven to compress a spring so that the first hole is completely in alignment with the second hole in order to facilitate bending of the knee.

5. A hydraulic system according to claim 1 wherein a chamber with a spring mounted thereon is adopted to receive the compressed oil, which can later be pushed back to its original position by means of the restitution force of the spring.

6. An artificial leg according to claim 1 wherein the foot is so connected to the ankle cap that one end of the pushing rod is received in the recess of the foot and the other end pushes against the transfer rod.

* * * * *